United States Patent [19]
Lambert et al.

[11] Patent Number: 5,552,133
[45] Date of Patent: Sep. 3, 1996

[54] METHOD OF MAKING ENCAPSULATED GAS MICROSPHERES USEFUL AS AN ULTRASONIC IMAGING AGENT

[75] Inventors: Karel J. Lambert, San Diego; Edward G. Jablonski, Escondido; Carl Hulle, San Diego, all of Calif.

[73] Assignee: Molecular Biosystems, Inc., San Diego, Calif.

[21] Appl. No.: 290,022

[22] Filed: Aug. 12, 1994

Related U.S. Application Data

[63] Continuation-in-part of Ser. No. 187,656, Jan. 26, 1994, abandoned, which is a continuation-in-part of Ser. No. 86,717, Jul. 2, 1993, abandoned.

[51] Int. Cl.$^6$ .................................................. A61K 49/00
[52] U.S. Cl. ................................ 424/9.52; 424/9.5
[58] Field of Search .............................. 424/9.52, 9.5

[56] References Cited

U.S. PATENT DOCUMENTS

| | | | |
|---|---|---|---|
| 4,572,203 | 2/1986 | Feinstein | 424/9 |
| 4,718,433 | 1/1988 | Feinstein | 424/9 |
| 4,957,656 | 9/1990 | Cerny et al. | 252/311 |
| 5,310,540 | 5/1994 | Giddy et al. | 424/9 |
| 5,393,524 | 2/1995 | Quay | 424/9.52 |
| 5,413,774 | 5/1995 | Schneider et al. | 424/9.51 |

FOREIGN PATENT DOCUMENTS

| | | |
|---|---|---|
| 0324938 | 7/1989 | European Pat. Off. . |
| 0458745 | 11/1991 | European Pat. Off. . |
| 0512693 | 11/1992 | European Pat. Off. . |
| 0554213 | 8/1993 | European Pat. Off. . |
| WO92/05806 | 4/1992 | WIPO . |
| WO9305819 | 4/1993 | WIPO . |

OTHER PUBLICATIONS

Ophir, J., et al., "Contrast agents in diagnostic ultrasound" *Ultrasound in Medicine* (1989) 15(4):319–333.
Echols, J. B., "Filtration of polymer viscosified fluids" *Adv. Filtr. Sep. Tech.* (1990) 1:108–110.
Young, F. R., *Cavitation* McGraw–Hill Book Company, London, (1989) pp. 4–6, 222–225.

*Primary Examiner*—Richard L. Raymond
*Assistant Examiner*—Mary C. Cebulak
*Attorney, Agent, or Firm*—Morrison & Foerster

[57] ABSTRACT

Encapsulated gas microspheres useful as an ultrasonic imaging agent are made by: mixing an aqueous solution of a heat-denaturable protein with a gas, and passing the gas-solution mixture through a mill whereby the mixture is emulsified near the denaturation temperature of the protein and subjected to mechanical shearing and cavitation which causes the formation of gas bubbles in the 0.1 to 10 micron range, and the protein to locally denature and deposit at the gas-liquid interface to form the encapsulated microspheres.

16 Claims, 3 Drawing Sheets

METHOD OF MAKING ENCAPSULATED GAS MICROSPHERES USEFUL AS AN ULTRASONIC IMAGING AGENT

CROSS-REFERENCE TO RELATED APPLICATIONS

This application is a continuation-in-part of application U.S. Ser. No. 08/187,656 filed Jan. 26, 1994 now abandoned which in turn is a continuation-in-part of U.S. Ser. No. 08/086,717 filed Jul. 2, 1993 now abandoned.

DESCRIPTION

1. Technical Field

This invention relates to ultrasonic imaging agents. More particularly it relates to a method of making encapsulated gas microspheres.

2. Background

Diagnostic ultrasonic imaging is based on the principle that waves of sound energy can be focused upon an area of interest and reflected in such a way as to produce an image thereof. An ultrasonic transducer is placed on a body surface overlying the area to be imaged, and ultrasonic energy in the form of sound waves is directed toward that area. The ultrasonic energy travels through the body and is reflected back to the transducer where it is translated into an ultrasonic image. The amount and characteristics of the reflected energy, and thus the image produced, depend upon the acoustic properties of the tissues and substances encountered. Changes in acoustic properties (e.g. variations in acoustic impedance) are most prominent at the interfaces of substances with different acoustic densities, such as liquid-solid or liquid-gas. These changes can enhance the reflection of ultrasonic energy and can be intensified by the proper use of a contrast agent.

Ophir and Parker (Ultrasound in Medicine and Biology 15(4):319–333 (1989)) describe several types of gaseous ultrasound contrast agents. The two principal types are gas bubbles suspended in a liquid (sometimes referred to as liquid-gas emulsions or foams, but hereinafter referred to as "microbubble suspensions") and encapsulated gases (commonly called "microspheres"). The present invention concerns a novel method for making microspheres.

Initially, microspheres were made by sonication. U.S. Pat. No. 4,572,203 describes the preparation of microspheres by subjecting biocompatible liquids to ultrasonic energy. U.S. Pat. No. 4,718,433 teaches the sonication of solutions of heat-denaturable proteins, such as human serum albumin, to produce more persistent microspheres. The present invention uses mechanical energy instead of ultrasound energy to make stable microspheres.

The mechanical energy employed by the present invention is in the form of shear forces. These forces are responsible for mechanically shearing a liquid-gas mixture to form a microbubble suspension, and also for causing hydrodynamic cavitation which releases energy. This energy can be absorbed by the surrounding liquid to effect localized protein denaturation and deposition at a gas-liquid interface to form discrete microspheres. Hydrodynamic cavitation can be distinguished from ultrasonic (acoustic) cavitation on the basis of the way in which each produces pressure variations on liquid systems which lead to the release of energy. In the former, pressure variations are produced by the rapid flow of a liquid through an orifice or across a surface, whereas in the latter, cycles of high frequency sound waves produce rapid local pressure variations. (See F. Ron Young. 1989 Cavitation Pages 4–5, McGraw-Hill Book Co. London). Additionally, hydrodynamic cavitation is produced in a flowing liquid, i.e., a liquid which is flowing through or across a stationary object. In comparison, acoustic cavitation is produced in a liquid system which must remain stationary through enough cycles of increasing and decreasing pressure (positive and suction pressure) to exhibit cavitation. Even in a continuous flow sonication system such as that described in U.S. Pat. No. 4,957,656, the residence time in an acoustic cavitation process makes it harder to control than in a true single-pass hydrodynamic cavitation system such as is described by the present invention.

Microbubble suspensions produced by mechanical shear forces are used per se as contrast agents or formed into microspheres by further processing. For instance, PCT Publication No. WO 92/05806 and U.S. Pat. No. 5,310,540 describes the preparation of a microbubble suspension, which they refer to as a "foam", of a filmogenic protein which is prepared by whipping a protein solution containing viscosifiers into a coarse foam at a constant temperature below that which would denature the protein. The resultant foam is then sheared mechanically to form bubbles of a desired range which are stabilized by the presence of the viscosifiers. The bubbles may then be further processed into microspheres by heat denaturation or by the addition of cross-linkers to harden the protein film surrounding the bubbles.

European Patent Application Pub. No. 0 458 745 A1 describes a process for making microspheres by forming an oil-in-water emulsion by mechanical shearing and simultaneously or subsequently adding a water-insoluble polymer which deposits at the interface. The hydrophobic phase is then evaporated to form air or gas filled microspheres.

The present invention relates to an improved method for making microspheres from heat-denaturable protein by subjecting a protein solution to mechanical shear forces. Such forces create a suspension of microbubbles that are simultaneously or subsequently encapsulated by a discrete shell. Because of the nature of cavitational heating, the denaturation of the protein is localized and forms the shell by depositing at the liquid-gas interface. This new method is easier to scale-up and leads to improved product yields as compared to the prior acoustic-based methods of making microspheres.

DISCLOSURE OF THE INVENTION

The invention is a method of making encapsulated gas microspheres useful as an ultrasonic imaging agent comprising:

a) providing an aqueous solution of a heat-denaturable protein at a temperature necessary to achieve incipient denaturation temperature during subsequent mechanical emulsification;

b) combining the solution with a gas;

c) emulsifying the protein solution and gas mixture by mechanically shearing the mixture to form a suspension of gas microbubbles having a mean diameter in the range of about 0.1 to about 10 microns; and d) encapsulating the gas microbubbles to form microspheres by mechanically cavitating the suspension to cause the protein to become denatured and thereby deposited at the gas-solution interface.

MODES FOR CARRYING OUT THE INVENTION

Figure 1:
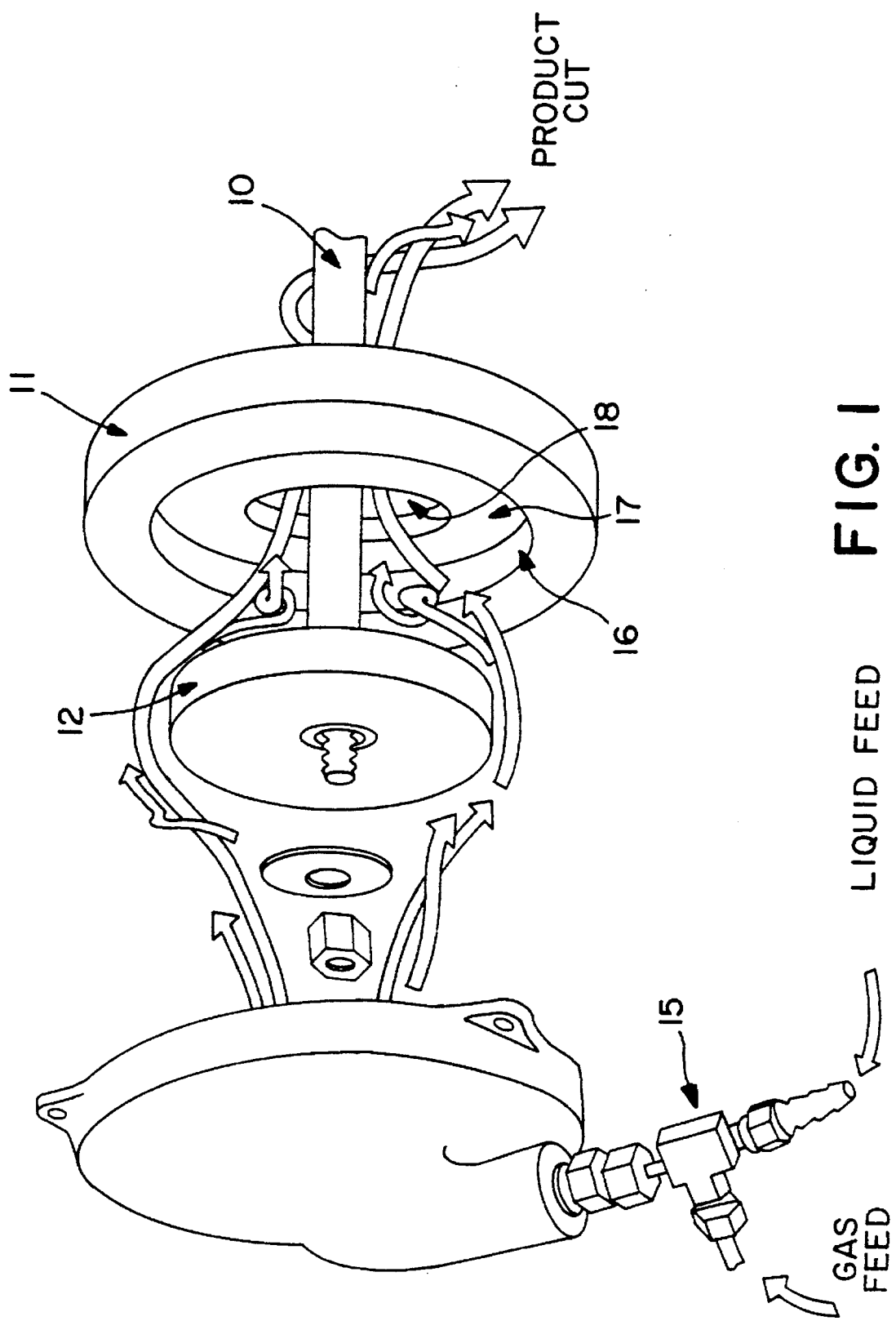
FIG. 1 is an exploded schematic view of one type of mill (a Gaulin mill) that may be used in the invention.

The invention process uses an aqueous solution of a heat-denaturable protein, i.e., its tertiary, and possibly also its secondary structure may be disrupted on heating resulting in the protein becoming water insoluble. The protein is filmogenic, denoting the ability to form a shell around gas when it is heat-denatured. Suitable proteins include naturally occurring proteins such as albumin, gamma-globulin (human), apo-transferrin (human), β-lactoglobulin and urease. Although the invention preferably employs a naturally occurring protein, synthetic proteins composed of an amino acid polymer (homopolymeric or heteropolymeric) which exhibit tertiary structure and are susceptible to heat denaturation may be used. Particularly well suited for the present invention is albumin and, more particularly, human serum albumin.

The denaturation temperature of the protein in solution will normally be in the range of 50° to 100° C. It can be obtained from tables of thermal protein denaturation in the literature, or experimentally by any known method. For example, to determine the denaturation temperature experimentally, a protein solution can be heated in a water bath while stirring. The denaturation temperature is the temperature at which insoluble material is first observed. Note that the denaturation temperature is affected by the nature, purity and source of the protein, the concentration of protein in the solution, the pH, buffer, ionic strength, the presence of stabilizers and the presence of chemical denaturants or detergents. Therefore, it is necessary to determine the denaturation temperature of the protein in the environment in which it will be employed to make microspheres. If desired, additives such as detergents or polar solvents can be employed to change the temperature at which denaturation takes place.

The following table gives the denaturation temperatures of several naturally occurring proteins which were determined experimentally as described above:

| PROTEIN | CONCEN-TRATION | pH | SOLVENT | $T_{denaturation}$ |
|---|---|---|---|---|
| Human Serum Albumin, USP Swiss Red Cross (Bern, Switzerland) | 50 mg/ml | 6.9 | 0.9% NaCl, 4 mM Sodium Caprylate, 4 mM Tryptophanate | 75° C. |
| Human Serum Albumin, USP Swiss Red Cross (Bern, Switzerland | 10 mg/ml | 6.9 | 0.9% NaCl, 1 mM Sodium Caprylate, 1 mM Tryptophanate | 78° C. |
| β-Lactoglobulin, Sigma (St. Louis, MO) | 25 mg/ml | 7.6 | USP Water | 90° C. |
| αβ-Globin, Sigma (St. Louis, MO) | 25 mg/ml | 5.0 | USP Water | 90° C. |
| Lysozyme Sigma (St. Louis, MO) | 100 mg/ml | 7.5 | 5 mm TRIS*, 2 mM DTT*** | 31° C. as determined immediately after addition of DTT |
| Human Gamma Globulin, acid pH method, Sigma (St. Louis, MO) | 40 mg/ml | 5.0 | 10 mM MES**, pH 5.0 | 66° C. |
| Human Gamma Globulin, alkaline pH method, Sigma (St. Louis, MO) | 40 mg/ml | 9.8 | 10 mM TRIS, pH 9.8 | 69° C. |
| apo-Transferrin, Sigma (St. Louis, MO) | 20 mg/ml | 7.5 | 10 mM TRIS* | 71° C. |

*TRIS = 2-amino-2-(hydroxymethyl)-1,3-propanediol
**MES = 2-(n-morpholino)ethanesulfonic acid
***DTT = dithiothreitol The protein may be chemically modified for the purpose of organ targeting (e.g. conjugated to an antibody) or quenching immunogenic activity (e.g. modification with polyethylene glycol). The protein is present in the solution at a concentration in the range of about 0.1 to 10% w/v, preferably about 1 to 5% w/v, and most preferably about 1% w/v.

Each apparatus employed to shear the protein solution/gas mixture will cause a certain amount of additional heating of the protein solution due to the mechanical shear forces exerted on the solution. That heat must be sufficient to cause localized denaturation of the protein at the gas-liquid interface. It is thus important to determine the amount of temperature increase caused by the apparatus so that the temperature at which the protein solution is introduced into the apparatus can be adjusted to achieve such local thermal denaturation. Specifically, the bulk temperature of the liquid in the apparatus must coincide with the incipient denaturation temperature immediately prior to cavitation. The cavitation event generates the additional heat necessary to locally denature the protein. Incipient denaturation temperature is defined as the temperature at which the protein is on the verge of denaturation, but the solution does not contain any denatured protein. This temperature is just below, typically 1° to 5° C. below, the denaturation temperature. If necessary, the starting protein solution may be preheated prior to being introduced into the apparatus to a temperature that allows the incipient denaturation temperature to be reached.

Once the proper starting temperature of the protein solution has been achieved, the solution is combined with a suitable gas, for example by introducing the gas into the protein solution prior to or during the emulsification step at a volume to volume ratio in the range of about 5% to 200% gas:liquid, preferably about 20% to 100%. The proper gas:liquid ratio will depend on the geometry of the apparatus, the physical characteristics of the gas (solubility, density, molecular weight, etc.), and can be adjusted to optimize output.

The gas to be used in the present invention need only be pharmacologically acceptable. Pharmacologically acceptable means the selected gas is biocompatible and has minimal toxicity to humans. The gas may be composed of a single compound or a mixture of compounds. Gases which have a limited solubility in water are preferred, although more soluble gases such as air, helium, argon, and nitrogen may be used. Insoluble gases include, but are not limited to, sulfur hexafluoride, perfluoroethane, perfluoropropane, perfluoromethane, and perfluorobutane. The solubility of a gas can be defined by determining the Bunsen Coefficient of the gas. This value is the volume of gas which is dissolved in a unit volume of water at a predetermined temperature and pressure. (See Wen, W.-Y., Muccitelli, J. A., J. Sol. Chem. 8:225–240 (1979)). The Bunsen Coefficient (measured in water at 25° C., l/atm) of the preferred insoluble gases is less than 0.01 mL/mL of solution.

When the method is used to make insoluble gas-filled miscrospheres the apparatus should be closed to the atmosphere so as to avoid introducing air into the mixture.

After the gas and protein solution are combined, the mixture is emulsified and subjected to cavitation under conditions that produce microspheres. This is accomplished using an apparatus in which mechanical shearing and hydrodynamic cavitation can be produced, such as high speed mixers, mills, fluidizers and the like. A preferred apparatus is a colloid mill which is defined as "a machine consisting of a high-speed rotor and a stator, dispension or emulsification being effected by the opposing faces." Advanced Filtration and Separation Technology, p.108–110. Examples of specific milling apparatuses which can be used are as follows:

Model #2½—Bemetek, Beverly, Mass.

Model W250V—Greerco, Hudson, New Hampshire

Model 2F—APV Gaulin, Everett, Massachusetts

Model L4R—Silverson, Chesham, UK

Model Polytron PT3000—Kinematica, Littaw, Switzerland

Figure 2:
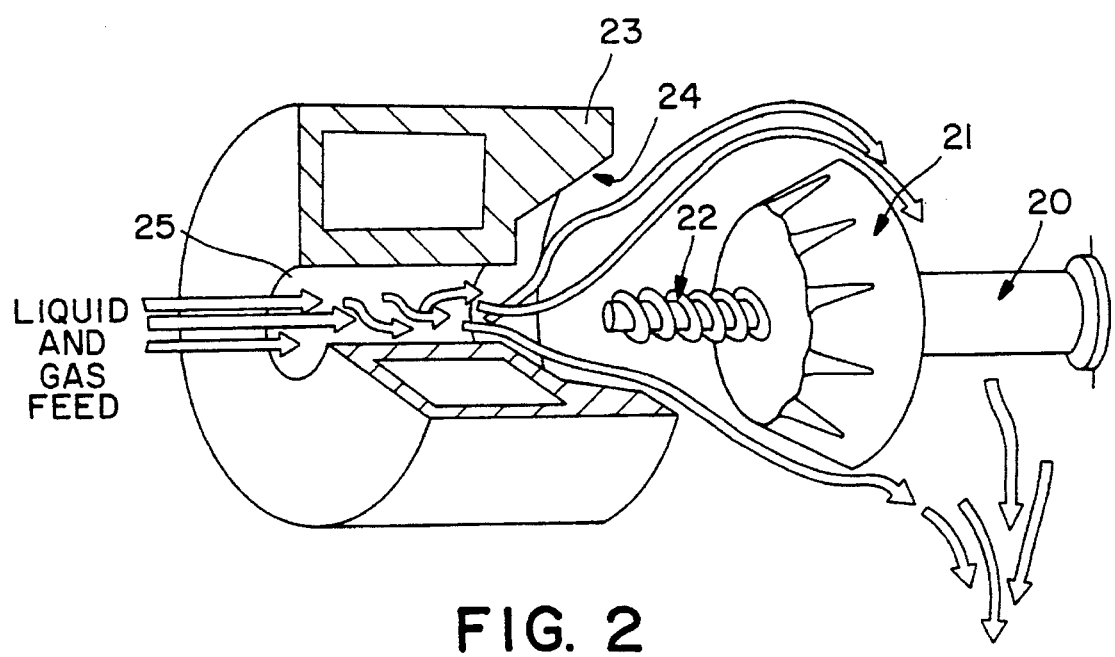
FIG. 2 is an exploded schematic view of another type of mill (a Bemetek mill) that may be used in the invention.
Figure 3:
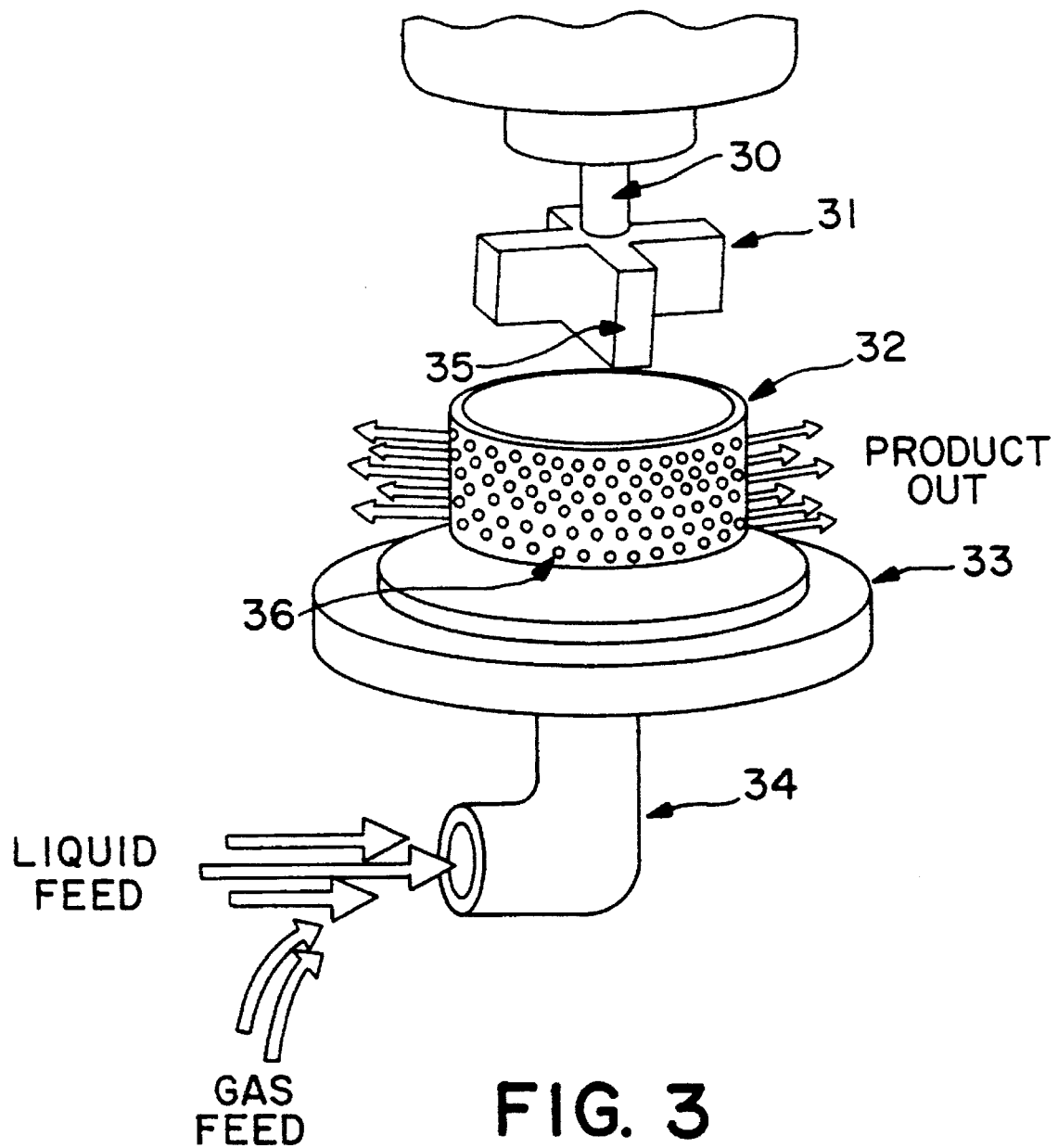
FIG. 3 is an exploded schematic view of still another type of mill (a Silverson mill) that may be used in the invention.

FIGS. 1–3 provide further details of several types of mills that may be used in the invention process.

FIG. 1 depicts the essential elements of a Gaulin mill. These are: a rotating shaft (10) operably connected to a motor (not shown); a disc rotor (12) affixed to the end of the shaft (10); and a stator (11). Stator (11) has a central bore opening (18) and a counterbore (16) into which the rotor is received. In this mill the protein solution and gas are fed through the mill via a "tee" (15). The protein solution/gas mixture is emulsified and cavitates between the surfaces of the rotor and stator. The "gap" in this mill is the space between radial surface (17) of the stator counterbore and the circumferential radial surface of the rotor. The temperature of the microsphere product will be taken (e.g. with a thermocouple, not shown) as the mixture exits past the stator (11).

FIG. 2 shows the essential elements of a Bemetek mill. This mill is similar in structure and function to the Gaulin mill of FIG. 1 —the main difference being the configurations of the rotor and the stator counterbore. It includes a rotary shaft (20) that carries a frustroconical rotor (21) that has a threaded leading end (22) and a stator (23) that has a central cylindrical opening (25) and a frustroconical counterbore (24) that is adapted to receive the rotor. The protein solution/gas mixture is fed into this mill via opening (25). The gas and solution are mixed as they pass by the threads on the shaft (22) and the mixture is emulsified and subjected to cavitation as it passes through the gap of the mill. The gap is defined by the space between the conical surfaces of the rotor and stator.

FIG. 3 illustrates a Silverson mill. The structure of this mill is quite different from those of the mills of Figs 1 and 2. The depicted Silverson mill has a rotating shaft (30) that carries a paddle blade rotor (31). The rotor is received in a cup-shaped perforated screen stator (32). The stator is mounted on a housing (33) fitted with an inlet fitting (34). The inlet fitting (34) extends up into the housing (33) opening at the bottom center of the perforated screen stator (32). The housing has a central opening (not shown) that communicates with the inlet fitting and with an opening (also not shown) in the bottom of the stator. In this mill the solution/gas is fed via the inlet fitting into the bottom of the stator and is emulsified and cavitated between the flat faces (35) of the paddle rotor and the inner cylindrical surface of the stator. The "gap" of this mill can be defined as the space between the rotor (31) and stator (32), but the effect of the gap size on the process is influenced by the size of the perforations (36) of the stator.

After passing through the mill the product may be cooled, typically to 10° –20° C, and defoamed by settling or by adding biocompatible defoaming agents that do not adversely affect the microspheres.

Passing the mixture through such a mill or equivalent device emulsifies and cavitates the mixture to form microspheres in the range of about 0.1 to 10 microns (mean diameter). Microspheresize may be determined by a suitable particle counter, for example a Coulter Multisizer II (Coulter Electronics, Hialeah, Fla.).

When using a mill such as those described in FIGS. 1–3, the rotor speed, gap size and gas:liquid ratio are the principal process parameters which affect the characteristics (mean size, size distribution, and Concentration of microspheres) of the microsphere product. Those parameters are adjusted empirically to provide a product having the desired characteristics. For any given product, its characteristics are defined clinically. For instance, putative specifications for air microspheres used for myocardial perfusions are: mean size, 4–6 microns; size distribution, 90% under 10 microns; concentration, $2-7\times10^8$ microspheres/mL.

The microspheres made by the present invention are echo reflective and of a size suitable for transpulmonary passage, (mean diameter less than 10 microns and greater than 0.1 microns). The size distribution may be altered by fractionation into larger or smaller microsphere populations. The microspheres may or may not be concentrated by removal of excess aqueous phase, or collected and resuspended in a second aqueous solution. Microspheres made by the process of the present invention are stable in suspension at 4° C. for at least 20 days, i.e., microsphere concentration does not decrease by more than 10%.

The invention is further illustrated by the following examples. These examples are not intended to limit the invention in any manner.

EXAMPLE 1

Process Temperature Monitoring and Control for Human Serum Albumin

As described above, the protein solution is pre-heated before processing so that the process temperature can reach and maintain the incipient denaturation temperature.

A typical method of practice is as follows:

A Model 2½" Bemetek Colloid Mill (FIG. 2; Bemetek Systems, Beverly Mass.), was piped so that the inlet port was connected to a heat exchanger. Gas impermeable tubing was used to make the soft connections between the heat exchanger hose barbs.

The outlet port from the process head was connected to a stainless steel post-process chiller.

Solution temperature was monitored at three sites (T1, T2 and T3). The T1 thermocouple was mounted in a Swagelok "Tee" between the pre-heat heat exchanger and the mill head to measure the feed temperature of the protein solution. A second "Tee" for introducing gas was also placed at the feed port. The T2 thermocouple was placed inside the exit from the process head, approximately 1 cm from the rotor and 2 cm from the shaft so that the temperature of the process could be accurately measured. In this way, the two temperatures can be measured independently, the feed temperature (T1) and the process temperature, (T2), and compared to determine the amount of heating of the solution during processing.

For this example, U.S.P. albumin was diluted with normal saline to make up a 1% (w/v) solution. The denaturation temperature was determined experimentally, as described, to be 78° C. It was fed into the mill at 200 mL/min following degassing along with perfluoropropane at 100 mL/min (50% v/v). Differences between T1 and T2 of 10° C. to 15° C. were noted. In order to obtain a process temperature of 77° C. (1° C. below denaturation temperature), the feed temperature was adjusted to a range of 62° C. to 67° C. Since the amount of heat generated will vary with different milling parameters, it is necessary to determine the difference between T1 and T2 with each change in milling parameters, (choice of mill, mill settings, flow rate, gas:liquid ratio, etc.) in order to target the process temperature to avoid bulk denaturation of the protein while successfully encapsulating the gas microbubbles with a thin shell of denatured protein. The chiller-out temperature (T3) was also monitored, and for best results was targeted at 20° C.

EXAMPLE 2

Method of Making Microspheres Containing Different Gases

Microspheres containing various gases were produced as follows: 5% human albumin solution (USP) was deaerated under continuous vacuum for two hours. The vacuum was released by filling the evacuated vessel with the gas of interest. Insoluble gases utilized include sulfur hexafluoride, perfluoroethane, and perfluoropropane. Microspheres containing more soluble gases, air, nitrogen, oxygen and argon, were also produced. The use of argon was representative of a high molecular weight, but relatively soluble, gas. The albumin solution was adjusted to 68° C. via an in-line heat exchanger and pumped at 100 mL/min into a 2½" colloid mill (Greerco, Hudson, N.H., model W250V or AF Gaulin, Everett, Mass., model 2F). The specific gas, at room temperature, was added to the liquid feed just upstream of the inlet port at a flow rate of 120–220 mL/min. The gap between the rotor and the stator was adjusted to 2/1000th inch and the albumin solution was milled continuously at about 7000 rpm at a process temperature of 73° C.

The dense white solution of microspheres thus formed was immediately chilled to a temperature of 10° C. by a heat exchanger, and collected in glass vials. The vials were immediately sealed. The material was characterized with regard to concentration and size distribution using a Coulter Counter. The results are shown in the Table below.

|  | Concentration (μ spheres/mL) | Mean Size (microns) |
| --- | --- | --- |
| Perfluoropropane | $8.3 \times 10^8$ | 3.8 |
| Perfluoroethane | $10.6 \times 10^8$ | 4.0 |
| Sulfur hexafluoride | $8.4 \times 10^8$ | 3.9 |
| Air | $9.2 \times 10^7$ | 3.4 |
| Nitrogen | $5.4 \times 10^7$ | 5.0 |
| Oxygen | $6.1 \times 10^7$ | 3.9 |
| Argon | $4.1 \times 10^7$ | 3.5 |

EXAMPLE 3

Effect of Rotor Speed and Gap Size

A 1% albumin solution was combined (200 mL/min) with perfluoropropane (100 mL/min) at a 50% gas to liquid (v/v) ratio. Microspheres were prepared according to the procedure described in Example 1 using different rotor tip speeds and gaps.

| Rotor Tip Speed (ft/min) | Gap (inches) | Concentration (μ spheres/mL) | Mean Size (microns) |
| --- | --- | --- | --- |
| 3500 | 0.005 | $0.76 \times 10^8$ | 13.4 |
| 4300 | 0.005 | $2.43 \times 10^8$ | 9.6 |
| 4800 | 0.005 | $9.38 \times 10^8$ | 3.8 |
| 9700 | 0.005 | $20.96 \times 10^8$ | 4.3 |
| 5200 | 0.008 | $12.87 \times 10^8$ | 5.0 |
| 7000 | 0.008 | $12.50 \times 10^8$ | 3.4 |
| 8700 | 0.008 | $14.42 \times 10^8$ | 3.0 |
| 9600 | 0.008 | $15.22 \times 10^8$ | 2.9 |

These results show that concentration increases and mean size decreases with increasing rotor speed while.

EXAMPLE 4

Effect of Gas to Liquid Ratio

A 0.5% Albumin solution (100 mL/min) was combined with perfluoropropane at 20, 50, 70 or 100 mL/min (20, 50, 70 or 100% gas to liquid v/v) using a Gaulin mill with an approximate gap of 0.012 and a rotor tip speed of 9950 ft/min. The data obtained are shown below:

| Gas/Liquid % (v/v) | Gap (inches) | Concentration (μ spheres/mL) | Mean Size (microns) |
| --- | --- | --- | --- |
| 20 | 0.012 | $6.54 \times 10^8$ | 3.6 |
| 50 | 0.012 | $7.51 \times 10^8$ | 4.3 |
| 70 | 0.012 | $8.76 \times 10^8$ | 5.0 |
| 100 | 0.012 | $8.66 \times 10^8$ | 5.9 |

These results show that both concentration and mean size increase with an increase in gas:liquid ratio.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method of making encapsulated gas microspheres useful as an ultrasonic imaging agent comprising:

a) providing an aqueous solution of a heat-denaturable protein at a temperature necessary to achieve incipient denaturation temperature during subsequent mechanical emulsification;

b) combining the solution with a gas;

c) emulsifying the protein solution and gas mixture by mechanically shearing the mixture to form a suspension of gas microbubbles having a mean diameter in the range of about 0.1 to about 10 microns; and d) encapsulating the gas microbubbles to form microspheres by mechanically cavitating the suspension to cause the protein to become denatured and thereby deposited at the gas-solution interface.

2. The method of claim 1 wherein said temperature is achieved by heating the solution.

3. The method of claim 1 wherein said temperature is achieved by including additives in the solution that alter the denaturation temperature of the protein.

4. The method of claim 1 wherein the protein is a naturally occurring protein.

5. The method of claim 4 wherein the protein is human serum albumin.

6. The method of claim 1 wherein the protein is a synthetic protein.

7. The method of claim 1 wherein the concentration of the protein in the solution is about 0.1 to 10% w/v.

8. The method of claim 1 wherein the concentration of the protein in the solution is about 1 to 5% w/v.

9. The method of claim 1 wherein the concentration of the protein in the solution is about 1% w/v.

10. The method of claim 1 wherein the gas is insoluble.

11. The method of claim 10 wherein the insoluble gas is sulfur hexafluoride, perfluoromethane, perfluoroethane, perfluoropropane, or perfluorobutane.

12. The method of claim 1 wherein the gas is air.

13. The method of claim 1 wherein the ratio of gas to protein solution is 5% to 200% v/v.

14. The method of claim 1 wherein the ratio of gas to protein solution is 20% to 100% v/v.

15. The method of claim 1 wherein steps (c) and (d) are effected by passing the mixture through a mill.

16. The method of claim 1 wherein the incipient denaturation temperature is about 1° to 5° C. below the denaturation temperature of the protein.

* * * * *